United States Patent [19]

Berg

[11] Patent Number: 5,228,957
[45] Date of Patent: Jul. 20, 1993

[54] SEPARATION OF METHYL T-BUTYL ETHER FROM CLOSE BOILING $C_5$ HYDROCARBONS BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 2,505

[22] Filed: Jan. 6, 1993

[51] Int. Cl.$^5$ .................. B01D 3/40; C07C 7/08; C07C 41/42
[52] U.S. Cl. ........................ 203/57; 203/58; 203/60; 203/62; 203/63; 203/64; 568/699; 585/856; 585/857; 585/860; 585/864; 585/865; 585/866
[58] Field of Search ............ 203/57, 58, 60, 62, 203/63, 64; 568/697, 699; 585/857, 856, 860, 862, 864, 865, 866

[56] References Cited

U.S. PATENT DOCUMENTS

| | | | |
|---|---|---|---|
| 4,148,695 | 4/1979 | Lee et al. | 203/63 |
| 4,513,153 | 4/1985 | Sandrin | 203/57 |
| 4,661,209 | 4/1987 | Berg | 203/58 |
| 5,160,414 | 11/1992 | Lee et al. | 568/699 |

*Primary Examiner*—Wilbur Bascomb, Jr.

[57] ABSTRACT

The separation by conventional distillation or rectification of methyl t-butyl ether from close boiling hydrocarbons is difficult because of the closeness of their vapor pressures. Methyl t-butyl ether can be readily separated from these by extractive distillation. Examples of effective agents are: from 1-pentene, dimethylsulfoxide; from cyclopentane, sulfolane and from n-pentane - cyclopentane mixtures, diethyl malonate.

3 Claims, No Drawings

SEPARATION OF METHYL T-BUTYL ETHER FROM CLOSE BOILING C₅ HYDROCARBONS BY EXTRACTIVE DISTILLATION

FIELD OF THE INVENTION

This invention relates to a method for separating methyl t-butyl ether from close boiling hydrocarbons by extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celcius degrees or higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Methyl t-butyl ether boils at 53° C. Hydrocarbons boiling close to methyl t-butyl ether are the paraffin n-pentane, B.P.=36° C.; the cycloparaffin cyclopentane, B.P.=50° C. and the olefin 1-pentene, B.P.=37° C. Extractive distillation would be an attractive method of effecting the separation of methyl t-butyl ether from close boiling hydrocarbons if agents can be found that (1) will enhance the relative volatility of methyl t-butyl ether from the close boiling hydrocarbons and (2) are easy to recover, that is, form no azeotrope with methyl t-butyl ether and boil sufficiently above methyl t-butyl ether to make separation by rectification possible with only a few theoretical plates.

Extractive distillation typically requires the addition of an equal amount to twice as much extractive agent as the methyl t-butyl ether - hydrocarbons on each plate of the rectification column. The extractive agent should be heated to about the same temperature as the plate into which it is introduced. Thus, extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. I recommend twenty Celcius degrees or higher difference. It is also desirable that the extractive agent be miscible with the methyl t-butyl ether - hydrocarbons otherwise it will form a two phase azeotrope with them and some other method of separation will have to be employed.

TABLE 1

Effect Of Relative Volatility On The Separation Of Methyl t-Butyl Ether From Hydrocarbons in 99% Purity

| Relative Volatility | Theoretical Plates | Actual Plates 75% Efficiency | Actual Plates, 75% Eff., Min. Reflux |
|---|---|---|---|
| 1.2 | 50 | 67 | 87 |
| 1.7 | 17 | 23 | 30 |
| 2.0 | 13 | 17 | 22 |
| 2.5 | 10 | 13 | 18 |
| 3.5 | 7 | 10 | 14 |

The advantage of employing an effective extractive distillation agent is shown in Table 1. Methyl t-butyl ether boils so close to n-pentane, cyclopentane or 1-pentene that the relative volatility between the methyl t-butyl ether and these three is less than 1.7. If extractive distillation is employed with an agent yielding a relative volatility of 3.5, a rectification column of only fourteen plates will be required to produce products of 99% purity. By ordinary rectification, 30 actual plates are required. Table 2 lists the relative volatility of methyl-t-butyl ether, 1-pentene and cyclopentane.

OBJECTIVE OF THE INVENTION

The objects of this invention are to provide a process or method of extractive distillation that will enhance the relative volatility of methyl t-butyl ether to close boiling hydrocarbons in their separation in a rectification column. It is a further object of this invention to identify organic compounds that are stable, can be separated from the close boiling hydrocarbons by rectification with relatively few plates and can be recycled to the extractive distillation column with little decomposition.

SUMMARY OF THE INVENTION

The objects of this invention are provided by a process for the separation of methyl t-butyl ether from close boiling hydrocarbons which entails the use of certain organic compounds as the agent in extractive distillation.

TABLE 2

Relative Volatility of Methyl t-Butyl Ether From Several Close Boiling Hydrocarbons

| Compounds | Relative Volatility |
|---|---|
| Cyclopentane | 1.55 |
| n-Pentane | 1.6 |
| 1-Pentene | 1.7 |

TABLE 3

Effective Agents For Separating Methyl t-Butyl Ether From Cyclopentane

| Compounds | Relative Volatility |
| --- | --- |
| Dimethylsulfoxide | 1.8 |
| Dimethylformamide | 2.0 |
| Sulfolane | 3.6 |
| 1-Methyl-2-pyrrolidinone | 1.8 |
| Adiponitrile | 2.9 |
| Acetophenone | 1.6 |
| t-Butanol | 2.2 |

TABLE 4

Effective Agents For Separating Methyl t-Butyl Ether From n-Pentane-Cyclopentane Mixtures

| Compounds | Relative Volatility Pnt/MTBE | CyP/MTBE |
| --- | --- | --- |
| Dimethylsulfoxide | 2.8 | 2.7 |
| Dimethylformamide | 4.7 | 2.3 |
| Sulfolane | 2.4 | 3.6 |
| Adiponitrile | 1.4 | 3.9 |
| 1-Methyl-2-pyrrolidinone | 3.9 | 1.8 |
| t-Butyl alcohol | 1.3 | 1.8 |
| Acetophenone | 1.7 | 1.7 |
| Dimethylacetamide | 3.5 | 1.9 |
| Diisobutyl ketone | 2.5 | 1.5 |
| Methyl isoamyl ketone | 2.8 | 1.7 |
| Isophorone | 2.8 | 1.5 |
| n-Propyl acetate | 2.6 | 1.8 |
| n-Hexyl formate | 1.6 | 1.6 |
| Ethyl acetate | 2.9 | 1.8. |
| Isopropyl acetate | 3.1 | 1.8 |
| Ethylene glycol diacetate | 3.3 | 1.8 |
| Diethyl carbonate | 3.1 | 1.8 |
| 1-Methoxy-2-propanol acetate | 3.3 | 1.9 |
| Ethyl isovalerate | 2.5 | 1.5 |
| Methyl benzoate | 1.8 | 1.6 |
| Methyl salicylate | 1.9 | 1.6 |
| Nitromethane | 1.5 | 1.6 |
| Nitroethane | 5.2 | 2.9 |
| 1-Nitropropane | 5.2 | 2.8 |
| 2-Nitropropane | 3.8 | 2.2 |
| 2,4-Pentanedione | 3.4 | 1.9 |
| Diethyl maleate | 3.4 | 1.8 |
| Diethyl malonate | 3.7 | 2.0 |
| Propylene glycol phenyl ether | 4.2 | 2.0 |
| Ethyl acetoacetate | 4.2 | 1.9 |
| Triacetin | 3.6 | 1.9 |

TABLE 5

Ineffective Agents For Separating Methyl t-Butyl Ether From n-Pentane-Cyclopentane Mixtures

| | |
| --- | --- |
| n-Butyl propionate | Isobutyl butyrate |
| Propyl caproate | Methyl heptanoate |
| Ethyl valerate | n-Butyl acetate |
| Anisole | |

TABLE 6

Effective Agents For Separating Methyl t-Butyl Ether From 1-Pentene

| Compounds | Relative Volatility |
| --- | --- |
| Dimethylsulfoxide | 3.9 |
| Sulfolane | 4.4 |
| Nitroethane | 3.0 |
| t-Butanol | 4.0 |
| Ethylene glycol diacetate | 5.5 |
| 1-Methoxy-2-propanol acetate | 3.5 |
| Methyl isoamyl ketone | 2.6 |
| Ethylene glycol methyl ether | 3.6 |
| Propylene glycol phenyl ether | 3.2 |
| Diethyl malonate | 3.1 |

TABLE 6-continued

Effective Agents For Separating Methyl t-Butyl Ether From 1-Pentene

| Compounds | Relative Volatility |
| --- | --- |
| Dimethylformamide | 3.0 |

DETAILED DESCRIPTION OF THE INVENTION

I have discovered that certain organic compounds will effectively increase the relative volatility between methyl t-butyl ether and close boiling hydrocarbons when employed as the agent in extractive distillation. The data in Tables 2-6 was obtained in a vapor-liquid equilibrium still.

Table 3 lists the compounds found to be effective extractive distillation agents to separate methyl-t-butyl ether from cyclopentane. They are dimethylsulfoxide, dimethylformamide, sulfolane, 1-methyl-2-pyrrolidinone, adiponitrile, acetophenone and t-butanol.

Table 4 lists the compounds found to be effective extractive distillation agents to separate methyl t-butyl ether from n-pentane-cyclopentane mixtures. They are dimethylsulfoxide, dimethylformamide, sulfolane, adiponitrile, 1- methyl 2-pyrrolidinone, t-butyl alcohol, acetophenone, dimethylacetamide, diisobutyl ketone, methyl isoamyl ketone, isophorone, n-propyl acetate, n-hexyl formate, ethyl acetate, isopropyl acetate, ethylene glycol diacetate, diethyl carbonate, 1-methoxy-2-propanol acetate, ethyl isovalerate, methyl benzoate, methyl salicylate, nitromethane, nitroethane, 1-nitropropane, 2-nitropropane, 2,4-pentanedione, diethyl maleate, diethyl malonate, propylene glycol phenyl ether, ethyl acetoacetate, and triacetin. With no agent the relative volatility is 1.4.

Table 5 lists the compounds that were found to be ineffective agents for separating methyl t-butyl ether from n-pentane - cyclopentane mixtures.

Table 6 lists the compounds found to be effective extractive distillation agents to separate methyl t-butyl ether from 1-pentene. They are dimethylsulfoxide, sulfolane, nitroethane, t-butanol, ethylene glycol diacetate, 1-methoxy-2-propanol acetate, methyl isoamyl ketone, ethylene glycol methyl ether, propylene glycol phenyl ether, diethyl malonate and dimethylformamide.

THE USEFULNESS OF THE INVENTION

The usefulness or utility of this invention can be demonstrated by referring to the data presented in Tables 2,,3,4 and 6. All of the successful agents show that methyl t-butyl ether can be separated from close boiling hydrocarbons by means of extractive distillation in a rectification column and that the ease of separation as measured by relative volatility is considerable.

WORKING EXAMPLES

Example 1: Thirty grams of methyl t-butyl ether, eleven grams of n-pentane, 15 grams of cyclopentane and 90 grams of dimethylsulfoxide were charged to the vapor-liquid equilibrium still and refluxed for eleven hours. Analysis indicated a vapor composition of 19.5% n-pentane, 33.7% cyclopentane, 46.8% methyl t-butyl ether; a liquid composition of 10.4% n-pentane, 18.5% cyclopentane, 71.1% methyl t-butyl ether which is a relative volatility of n-pentane to methyl t-butyl ether of 2.8 and cyclopentane to methyl t-butyl ether of 2.7.

Example 2: Forty grams of cyclopentane, 20 grams of methyl t-butyl ether and 60 grams of sulfolane were charged to the vapor-liquid equilibrium still and refluxed for four hours. Analysis indicated a vapor composition of 76.3% cyclopentane, 23.7% methyl t-butyl ether; a liquid composition of 47.2% cyclopentane, 52.8% methyl t-butyl ether which is a relative volatility of 3.6.

Example 3 : Forty-five grams of methyl t-butyl ether, five grams of 1-pentene and 50 grams of dimethylsulfoxide were charged to the vapor-liquid equilibrium still and refluxed for two hours. Analysis indicated a vapor composition of 9.9% 1-pentene, 90.1% methyl t-butyl ether; a liquid composition of 2.7% 1-pentene, 97.3% methyl t-butyl ether which is a relative volatility of 3.9.

I claim:

1. A method for recovering methyl-t-butyl ether from a mixture of methyl t-butyl ether and 1-pentene which comprises distilling a mixture of methyl t-butyl ether and 1-pentene in the presence of about one part of an extractive agent per part of methyl t-butyl ether - 1-pentene mixture, recovering the 1-pentene as overhead product and obtaining the methyl t-butyl ether and the extractive agent from the stillpot, wherein said extractive agent consists of one material selected from the group consisting of sulfolane, nitroethane, t-butanol, ethylene glycol diacetate, 1-methoxy-2-propanol acetate, methyl isoamyl ketone, ethylene glycol methyl ether, propylene glycol phenyl ether and diethyl malonate.

2. A method for recovering methyl t-butyl ether from a mixture of methyl t-butyl ether and cyclopentane which comprises distilling a mixture of methyl t-butyl ether and cyclopentane in the presence of about one part of an extractive agent per part of methyl t-butyl ether - cyclopentane mixture, recovering cyclopentane as overhead product and obtaining the methyl t-butyl ether and the extractive agent from the stillpot, wherein said extractive agent consists of one material selected from the group consisting of sulfolane, adiponitrile and t-butanol.

3. A method for recovering methyl t-butyl ether from a mixture of methyl t-butyl ether, n-pentane and cyclopentane which comprises distilling a mixture of methyl t-butyl ether, n-pentane and cyclopentane in the presence of about one part of an extractive agent per part of methyl t-butyl ether - n-pentane - cyclopentane mixture, recovering n-pentane and cyclopentane as overhead products and obtaining the methyl t-butyl ether and the extractive agent from the stillpot, wherein said extractive agent consists of one material selected from the group consisting of sulfolane, adiponitrile, t-butyl alcohol, acetophenone, methyl isoamyl ketone, isophorone, n-propyl acetate, n-hexyl formate, ethyl acetate, isopropyl acetate, ethylene glycol diacetate, diethyl carbonate, 1-methoxy-2-propanol acetate, ethyl isovalerate, methyl benzoate, methyl salicylate, nitromethane, nitroethane, 1-nitropropane, 2-nitropropane, 2,4-pentanedione, diethyl maleate, diethyl malonate, propylene glycol phenyl ether, ethyl acetoacetate and triacetin.

* * * * *